United States Patent
Garcia Tello (10) Patent No.: US 8,987,003 B2
(45) Date of Patent: Mar. 24, 2015

(54) BIOSENSOR DEVICE AND METHOD OF DETECTING BIOLOGICAL PARTICLES

(75) Inventor: Pablo Garcia Tello, Leuven (BE)

(73) Assignee: NXP B.V., Eindhoven (NL)

( * ) Notice: Subject to any disclaimer, the term of this patent is extended or adjusted under 35 U.S.C. 154(b) by 566 days.

(21) Appl. No.: 12/740,750

(22) PCT Filed: Nov. 4, 2008

(86) PCT No.: PCT/IB2008/054578
§ 371 (c)(1),
(2), (4) Date: Apr. 30, 2010

(87) PCT Pub. No.: WO2009/060379
PCT Pub. Date: May 14, 2009

(65) Prior Publication Data
US 2010/0248391 A1 Sep. 30, 2010

(30) Foreign Application Priority Data
Nov. 6, 2007 (EP) .................................... 07120056

(51) Int. Cl.
*G01N 33/566* (2006.01)
*G01N 21/552* (2014.01)
*G01N 21/77* (2006.01)

(52) U.S. Cl.
CPC .......... *G01N 21/552* (2013.01); *G01N 21/7746* (2013.01); *Y10S 436/805* (2013.01); *Y10S 435/808* (2013.01)
USPC ........... 436/518; 436/524; 436/527; 436/164; 436/805; 435/288.7; 435/808; 385/15

(58) Field of Classification Search
None
See application file for complete search history.

(56) References Cited

U.S. PATENT DOCUMENTS

| | | | |
|---|---|---|---|
| 3,814,499 A | * | 6/1974 | Marcatili ....................... 385/123 |
| 6,583,399 B1 | | 6/2003 | Hunziker et al. |
| 6,781,696 B1 | * | 8/2004 | Rosenberger et al. ........ 356/437 |
| 2002/0097401 A1 | * | 7/2002 | Maleki et al. .................. 356/436 |

(Continued)

FOREIGN PATENT DOCUMENTS

WO 01/40757 A 6/2001

OTHER PUBLICATIONS

Vollmer, F., et al; "Multiplexed DNA Quantification by Spectroscopic Shift of Two Microsphere Cavities"; Biophysical Journal; New York, New York, US; vol. 85; p. 1974-1979 (Sep. 1, 2003).

(Continued)

*Primary Examiner* — Chris L Chin
*Assistant Examiner* — Richard Moerschell (57) ABSTRACT

A biosensor device (100) for detecting biological particles, the biosensor device (100) comprising an electromagnetic radiation transmitting member (102) adapted for transmitting electromagnetic radiation and a plurality of sensor active structures (104) arranged at the electromagnetic radiation transmitting member (102), wherein each of the plurality of sensor active structures (104) is sensitive to specific biological particles and is adapted to modify electromagnetic radiation transmission properties of the electromagnetic radiation transmitting member (102) in the event of the presence of the respective biological particles, and wherein the electromagnetic radiation transmitting member (102) is adapted for a simultaneous detection of different biological particles at different ones of the plurality of sensor active structures (104).

9 Claims, 5 Drawing Sheets (56) References Cited

U.S. PATENT DOCUMENTS

2003/0021301 A1* 1/2003 Vahala et al. ............. 372/3
2003/0174923 A1 9/2003 Arnold et al.
2004/0146431 A1* 7/2004 Scherer et al. .......... 422/82.05
2004/0238744 A1* 12/2004 Arnold et al. ........... 250/341.2

OTHER PUBLICATIONS

Hanumegowda, N. M., et al; "Development of Label-Free Microsphere Optical Resonator Bio/Chemical Sensors"; Proc. SPIE; vol. 6004; 12 Pages (2005).

Drmanac, Radoje, et al; "Sequencing by Hybridization (SBH): Advantages, Achievements, and Opportunities"; Advanced Biochemical Engineering/Biotechnology, vol. 77; (2002).

Arnold, S., et al; "Shift of Whispering-Gallery Modes in Microspheres by Protein Adsorption"; Optics Letters, vol. 28, No. 4; 3 Pages (Feb. 15, 2003).

International Search Report and Written Opinion for Application PCT/IB2008/054578 (May 14, 2009).

* cited by examiner

BIOSENSOR DEVICE AND METHOD OF DETECTING BIOLOGICAL PARTICLES

FIELD OF THE INVENTION

The invention relates to a biosensor device.

Moreover, the invention relates to a method of detecting biological particles.

BACKGROUND OF THE INVENTION

A biosensor may be denoted as a device that may be used for the detection of an analyte that combines a biological component with a physicochemical or physical detector component.

For instance, a biosensor may be based on the phenomenon that capture molecules immobilized on a surface of a biosensor may selectively hybridize with target molecules in a fluidic sample, for instance when an antibody-binding fragment of an antibody or the sequence of a DNA single strand as a capture molecule fits to a corresponding sequence or structure of a target molecule. When such hybridization or sensor events occur at the sensor surface, this may change the electrical or optical properties of the surface that can be detected as the sensor event.

US 2003/0174923 discloses detecting and/or measuring a substance based on a resonance shift of photons orbiting within a microsphere of a sensor. Since the resonance of the microsphere has a large quality factor, the sensor is sensitive. The sensor includes the microsphere coupled with at least one optical fiber. The surface of the microsphere includes receptors complementary to the substance. The at least one optical fiber can be provided with at least one additional microsphere having a surface free of the receptors. Resonance shifts observed in such an additional microsphere(s) can be attributed to factors unrelated to the presence of the substance. The resonance shift observed in the microsphere with the receptors can be compensated based on the resonance shift of the additional microsphere(s) to remove the influence of these other factors.

Vollmer et al. (2003), "Multiplexed DNA Quantification by Spectroscopic Shift of Two Microsphere Cavities", Biophysical Journal, Volume 85, pp. 1974-1979 discloses a spectroscopic technique for high-sensitivity, label-free DNA quantification. An optical resonance (whispering gallery mode) excited in a micron-sized silica sphere can be used to detect and measure nucleic acids. The surface of the silica sphere is chemically modified with oligonucleotides. Hybridization to the target DNA leads to a red shift of the optical resonance wavelength. Furthermore, each microsphere can be identified by its unique resonance wavelength. DNA detection is demonstrated by using two microspheres. The multiplexed signal from two microspheres allows to discriminate a single nucleotide mismatch in an 11-mer oligonucleotide with a high signal-to-noise ratio of 54. This all-photonic whispering gallery mode biosensor can be integrated on a semiconductor chip that makes it an easy to manufacture, analytic component for a portable, robust lab-on-a-chip device.

Conventional biosensor chips based on whispering gallery modes may require a measurement that takes a comparatively long amount of time.

OBJECT AND SUMMARY OF THE INVENTION

It is an object of the invention to provide a biosensor having a sufficient performance.

In order to achieve the object defined above, a biosensor device and a method of detecting biological particles according to the independent claims are provided.

According to an exemplary embodiment of the invention, a biosensor device for detecting biological particles is provided, the biosensor device comprising an electromagnetic radiation transmitting member (such as a waveguide) adapted for transmitting electromagnetic radiation and a plurality of sensor active structures (such as microspheres) arranged at the electromagnetic radiation transmitting member, wherein each of the plurality of sensor active structures is sensitive to specific biological particles (for instance by a biosensing functionalization at a surface of the microspheres) and is adapted to modify electromagnetic radiation transmission properties of the electromagnetic radiation transmitting member (for instance for triggering a frequency shift of the electromagnetic radiation, for instance a red shift) in the event of the presence of the respective biological particles (for instance due to hybridization events between capture molecules immobilized on the microspheres and complementary biomolecules), wherein the electromagnetic radiation transmitting member is adapted for a simultaneous (i.e. parallel in time) detection of different biological particles at different ones of the plurality of sensor active structures (for instance by a simultaneous measurement of multiple separate electromagnetic radiation beams propagating without crosstalk through the electromagnetic radiation transmitting member, for instance through multiple optical fibers arranged in parallel).

According to another exemplary embodiment of the invention, a method of detecting biological particles is provided, the method comprising transmitting electromagnetic radiation along an electromagnetic radiation transmitting member having attached thereto a plurality of sensor active structures, wherein each of the plurality of sensor active structures is sensitive to specific biological particles, and simultaneously detecting different biological particles at different ones of the plurality of sensor active structures by evaluating modified electromagnetic radiation transmission properties of the electromagnetic radiation transmitting member in the event of the presence of the respective biological particles at a respective one of the plurality of sensor active structures.

The term "biosensor" may particularly denote any device that may be used for the detection of an analyte comprising biological molecules such as DNA, RNA, proteins, enzymes, cells, bacteria, virus, etc. A biosensor may combine a biological component (for instance capture molecules at a sensor active surface capable of detecting molecules) with a physicochemical or physical detector component (for instance a waveguide having transmission properties which is modifiable by a sensor event).

The term "biological particles" may particularly denote any particles which play a significant role in biology or in biological or biochemical procedures, such as genes, DNA, RNA, proteins, enzymes, cells, bacteria, virus, etc.

The term "sensor active region" may particularly denote an exposed region of a sensor, for instance of a spherical structure such as a silica microsphere, which may be brought in interaction with a fluidic sample so that a detection event may occur in the sensor active region. In other words, the sensor active region may be the actual sensitive area of a sensor device, in which sensitive area processes take place forming the basis of the sensing.

The term "fluidic sample" may particularly denote any subset of the phases of matter. Such fluids may include liquids, gases, plasmas and, to some extent, solids, as well as mixtures thereof. Examples for fluidic samples are DNA containing fluids, blood, interstitial fluid in subcutaneous tissue, muscle or brain tissue, urine or other body fluids. For instance, the fluidic sample may be a biological substance. Such a substance may comprise proteins, polypeptides, nucleic acids, DNA strands, etc.

The term "electromagnetic radiation" may particularly denote a beam of photons of any appropriate wavelength. This may include the optical spectrum (for instance the range between 400 nm and 800 nm), but may also include electromagnetic radiation of other wavelengths, like UV, infrared, microwaves, or even X-rays. According to exemplary embodiments of the invention, such electromagnetic radiation may be used as a probe, since this electromagnetic radiation is directed through a structure such as an optical fiber and may be brought in interaction with a sensor component attached to an outer surface of the optical fiber.

The term "whispering gallery modes" may particularly denote a phenomenon that may occur at particular resonant wavelengths of light confined to a cylindrical or spherical volume with an index of refraction greater than that surrounding it. At these wavelengths, the light undergoes total internal reflection at the volume surface and becomes trapped within the volume for timescales of the order of nanoseconds. According to exemplary embodiments, the cylindrical or spherical volume may be coupled to, for instance adhered to, an exposed surface of an optical fiber.

The term "electromagnetic radiation transmitting member" may particularly denote any component, for instance a purely optical or an optoelectronic component, which is capable of transmitting electromagnetic radiation along a predefined path. For instance, the electromagnetic radiation transmitting member may define an optical path by providing a structure having a refractive index larger than one. For a specific wavelength and a specific geometry of the electromagnetic radiation transmitting member in combination with its refractive index, total refraction may be initiated at a border between the electromagnetic radiation transmitting member and the surrounding air or vacuum. This may ensure that the electromagnetic radiation beam is securely guided along a predefined path of the biosensor device to be selectively brought in interaction with one of the plurality of sensor active structures. For example, the electromagnetic radiation transmitting member may be a flat planar cuboid through which a plurality of electromagnetic radiation beams can be guided independently from one another, i.e. without crosstalk. Alternatively, the electromagnetic radiation transmitting member may comprise a plurality of, for instance parallel aligned, optical fibers, each of the fibers being adapted to guide a light beam through the fiber.

The term "simultaneous detection of different biological particles at different ones of the plurality of sensor active structures" may particularly denote that the arrangement, particularly the localization, of sub-components of the electromagnetic radiation transmitting member is specifically configured in a manner that an independent detection at each individual one of the several sensor active structures is enabled. For example, a light beam serving as a probe for such a detection of one sensor active structure may be brought in interaction with exactly one of the multiple sensor active structures so as to allow for a detection at another one of the sensor active structures using another electromagnetic radiation beam at the same time.

According to an exemplary embodiment of the invention, a biosensing component may be provided having multiple (for instance at least ten, particularly at least one hundred, more particularly at least one thousand) sensor active structures (such as spherical microstructures made of silica) being functionalized with a sensor active material. The sensor active structures may be attached (for instance by adhering, welding, mechanically fixing) at different and distinguishable positions of an electromagnetic radiation transmitting member (for instance formed by an array of optical fibers) with such a design that a simultaneous detection of different fractions of biomolecules at different sensor active structures is enabled. For example, different biological probes may be immobilized at a surface of each of the sensor active structures (for instance capture molecules being complementary to biological particles under detection). This may allow for a massive parallel and therefore fast detection architecture allowing for a significantly accelerated detection mechanism. Moreover, due to a spatial separation of different sensor active structures, a functionalization procedure may be simplified, since it may be possible to simply immerse the different sensor active structures in different functionalizing solutions, for instance at the same time. Therefore, a biosensor array may be provided which comprises many optical fibers having a sensor structure contacted thereto each of which being sensitive for a specific biological particle which is complementary to the respective sensor structure.

Next, further exemplary embodiments of the biosensor device will be explained. However, these embodiments also apply to the method.

The electromagnetic radiation transmitting member may comprise a plurality of spatially separated electromagnetic radiation transmitting units, each of the plurality of sensor active structures being arranged at an assigned one of the plurality of spatially separated electromagnetic radiation transmitting units. By spatially separating the electromagnetic radiation guiding structures from one another, undesired crosstalk between different probing beams may be securely prevented, thereby allowing for a highly accurate and parallel detection scheme. Spatially separating may also include functionally decoupling the electromagnetic radiation transmitting property of the individual electromagnetic radiation transmitting unit. In other words, electromagnetic radiation propagating through one of the electromagnetic radiation transmitting units may be prevented from propagating through another one of the electromagnetic radiation transmitting units. This may allow for a clear distinction of the propagation paths, thereby allowing for an unambiguous assignment of detection signals and detection events.

The plurality of spatially separated electromagnetic radiation transmitting units may be a plurality of different (electromagnetic) waveguides. A waveguide may be denoted as a structure which guides electromagnetic waves such as light. Waveguides can be constructed to carry waves over a wide portion of the electromagnetic spectrum, but may be especially useful in the optical or microwave frequency ranges. Depending on the frequency, they can be constructed from conductive or dielectric materials.

The plurality of spatially separated electromagnetic radiation transmitting units may comprise a plurality of optical fibers, each of the plurality of sensor active structures being arranged at an assigned one of the plurality of optical fibers. An optical fiber may be a glass or plastic fiber (which may be made of silica glass) designed to guide light along its length. Fibers may be denoted as an optical analogon to metal wires because they allow optical signals to propagate along them with low loss. Particularly, such a fiber may comprise a core and a confinement and may be based on total internal reflection.

Particularly, when the plurality of optical fibers are arranged in parallel, a detection along a predefined direction is made possible and it may be possible to share an electromagnetic radiation source (such as a laser) and/or an electromagnetic radiation detector (such as a photodiode, an array of photodiodes or a CCD, "charge coupled device"). Furthermore, a parallel alignment of optical fibers may be easy in manufacture and may allow for a compact design.

Each of the plurality of sensor active structures may comprise a microbody, particularly a microsphere, more particularly a silica microsphere. Thus, a body having dimensions for instance in the order of magnitude of micrometers or less to millimeters or more may be simply attached to an outer surface of a, for instance, cylindrical waveguide such as an optical fiber. More specifically, the spheres may be coupled evanescently to the optical fiber. Fiber-sphere coupling and sphere fabrication can be performed, according to exemplary embodiments of the invention, as described by Vollmer et al. (2003), "Multiplexed DNA Quantification by Spectroscopic Shift of Two Microsphere Cavities", Biophysical Journal, Volume 85, p. 1975, right column, which is herewith incorporated by reference in the disclosure of the present application. With electromagnetic radiation such as light traveling along the waveguide, an interaction between the electromagnetic radiation and the functionalized microbody may be promoted, so that a transmission property of the electromagnetic radiation beam may depend sensitively on possible interactions between the sensor active structures and components of a fluidic sample, thus allowing to determine components of a sample qualitatively or quantitatively. For example, hybridization events between capture molecules immobilized on an outer surface of the microbody and particles of an analyte under analysis may result in a characteristic pattern of the electromagnetic radiation transmission scheme. The microbody can have a spherical structure, may have an ellipsoid structure, may have a cylindrical structure, may have a cuboid structure, or the like. However, the microbody may be designed and shaped according to exemplary embodiments of the invention in a manner that whispering gallery modes (WGM) may be excited at or in the microbody, which may serve as a basis for a detection scheme.

The biosensor device may comprise one or more electromagnetic radiation sources adapted for generating electromagnetic radiation to be coupled into the electromagnetic radiation transmitting member. Such an electromagnetic radiation source may be a laser, particularly a semiconductor laser such as a laser diode. Such a laser diode may be provided in common for all or a part of the optical fibers, wherein one or more optical element such as mirrors, lenses, apertures, beam splitters, optical couplers, diffusers, etc. may be used for directing the light into the fibers. Alternatively, a separate laser diode may be provided for individual ones of the optical fibers. Also light emitting diodes may be implemented as electromagnetic radiation source.

The biosensor device may further comprise one or more electromagnetic radiation detectors adapted for detecting electromagnetic radiation after propagation along the electromagnetic radiation transmitting member. Such an electromagnetic radiation detector may comprise one or more photodiodes, or may comprise a two-dimensional or one-dimensional detector array such as a CCD (charge coupled device). An electromagnetic radiation detector may be provided in common for two or more of the optical fibers, or may be provided separately for each individual one of the optical fibers.

The biosensor device may be adapted as a DNA (desoxyribonucleic acid) sequencing biosensor device. The term "DNA sequencing" may denote a procedure that determines the order of base pairs in a segment of DNA. In other words, it may denote the experimental process of determining the nucleotide sequence in a region of DNA. DNA sequencing may encompass biological methods for determining the order of the nucleotide basis, adenine, guanine, cytosine, and thymine in a DNA oligonucleotide.

The biosensor device may be adapted for sequencing the biological particles by hybridization events between the plurality of sensor active structures and the biological particles. By immobilizing capture molecules at an outer surface of the microbodies, which capture molecule functionalization may then serve as the sensor active structure, and by subsequently bringing a fluidic sample possibly comprising the biological particles in functional contact with the functionalized surface of the microbodies, in the case of complementary of sequences of the capture molecules and the particles to be detected, so-called hybridization events may occur in a very selective manner. In other words, when a specific modification in the transmitted electromagnetic radiation transmission scheme is detected (for instance based on whispery gallery modes), it can be concluded that hybridization events have occurred between complementary capture molecules and biological particles. By foreseeing different capture molecules at different sensor active structures, the sequence of particles to be detected can be analyzed or any fluid separation or fluid analysis technique may be carried out.

Particularly, the biosensor device may be adapted for a multiplexed detection of different biological particles at different ones of the plurality of sensor active structures. For example, one or more multiplexers may be provided which may be connected to the various optical fibers in such a manner that a multiplexed detection and evaluation is possible.

The biosensor device may be adapted for a simultaneous detection of different biological particles based on a whispering gallery mode detection. As already explained above, the phenomenon of whispering gallery mode is disclosed, as such, in US 2003/0174923 A1 or US 2002/0097401 A1, which are both incorporated by reference in the disclosure of the present patent application.

The biosensor device may comprise one or more capture molecules arranged at a surface of each of the plurality of sensor active structures being adapted for interacting with the biological particles. Thus, the capture molecules may be different for different ones of the sensor active structures so that a massive parallel analysis of a fluidic sample may be performed with the result that at specific fibers, where capture molecules having a complementary sequence to fractions of the biological particles are present, sensor events may be detected by an optoelectronic way.

According to an exemplary embodiment of the invention, a method for a DNA sequencing by hybridization may be provided. Particularly, a method to perform label-free DNA sequencing using a technology that can be fabricated using conventional CMOS processing is provided.

Sequencing by hybridization (SBH) may be denoted as a class of methods for determining the order in which nucleotides occur on a strand of DNA. This procedure may be typically used for looking for small changes relative to a known DNA sequence. The binding of one strand of DNA to its complementary strand and the DNA double helix (aka hybridization) may be sensitive to even single-base mismatches when the hybrid region is short or if specialized mismatch detection proteins are present. This may be exploited in a variety of ways, for instance via DNA chips or microarrays with thousands to billions of synthetic oligonucleotides found in a genome of interest plus many known variations or even all possible single-base variations. However, such conventional SBH techniques includes several drawbacks, such as that sample preparation in hybridization chips is costly and slow, highly skilled workers are needed for sample preparation, detection levels require PCR (polymerase chain reaction) amplification of DNA, labeling for readout is costly and subjected to errors.

In view of these recognitions, the present inventor has recognized that another technique as disclosed herein is more reliable, may increase the sensitivity so that only minimum or no PCR amplification is required, may avoid the use of labels for detection to obtain a cost reduction, may be easily integratable with CMOS technology, may avoid false readout due to label detection, and may obtain a high simplification of the sample preparation procedure.

In order to obtain these and other advantages, embodiments of the present invention may make use of the whispering gallery mode (WGM) detection method. Whispering gallery mode (WGM) may be denoted as a particularly mode of micro-cavity resonances. It may occur when light at certain frequencies travels in a dielectric medium of circular geometry. After repeated total internal reflections at a curve boundary, an electromagnetic field can close on itself, giving rise to resonances. Particularly, the use of the WGM technique for DNA sequencing may be made possible according to exemplary embodiments of the invention.

This may allow for DNA sequencing, more particularly sequencing by hybridization. According to an exemplary embodiment, a multiplexing capability for DNA sequencing may be provided. For this purpose, microbodies may not or not only be provided in series to a same optical fiber, but may be arranged at different (for instance parallel aligned) optical fibers which are optically decoupled from one another. Thus, a variety of specifically coded spheres may be provided arranged in parallel to a network of optical fibers in order to provide a (multiplexed) method that allows DNA sequencing.

Therefore, according to exemplary embodiments of the invention, no sequential detection, or not only a sequential detection may be performed, but coating and discrimination may be performed at least partially in parallel due to the geometrical arrangements of various exemplary embodiments of the invention.

By providing an optical fiber having different branches each having attached thereto one or more microbodies coated with different oligonucleotides, it may become possible to coat different spheres at the same time because they are coupled to different optical fibers and in different fluidic channels. Each channel may have a different inlet where the different coatings may be introduced. Thus, it may be determined beforehand which DNA strand goes to which sphere. Furthermore, such a geometry may allow to measure at the same time all those spheres.

The biosensor may be manufactured in CMOS technology. CMOS technology allow to manufacture structures with very small dimensions so that (spatial) accuracy of the device will be improved by implementing CMOS technology. A BiCMOS process may be used as well, wherein BiCMOS in fact is a CMOS process with some additional processing steps to add bipolar transistors. The same holds for CMOS processes with other embedded options like embedded flask, embedded DRAM, etc. In particular this may be relevant because the presence of an option often provides opportunities to use additional materials that come with the options "at zero cost". For instance, an appropriate high-k material (an insulating material with a high dielectric constant, for example aluminium-oxide) that comes with an embedded DRAM process can be used "at zero cost" for any desired purpose.

The biosensor device may be monolithically integrated in a semiconductor substrate, particularly comprising one of the group consisting of a group IV semiconductor (such as silicon or germanium), and a group III-group V semiconductor (such as gallium arsenide).

The biosensor chip or microfluidic device may be or may be part of a sensor device, a sensor readout device, a lab-on-chip, an electrophoresis device, a sample transport device, a sample mix device, a sample washing device, a sample purification device, a sample amplification device, a sample extraction device or a hybridization analysis device. Particularly, the biosensor or microfluidic device may be implemented in any kind of life science apparatus.

For any method step, any conventional procedure as known from semiconductor technology may be implemented. Forming layers or components may include deposition techniques like CVD (chemical vapour deposition), PECVD (plasma enhanced chemical vapour deposition), ALD (atomic layer deposition), or sputtering. Removing layers or components may include etching techniques like wet etching, plasma etching, etc., as well as patterning techniques like optical lithography, UV lithography, electron beam lithography, etc.

Embodiments of the invention are not bound to specific materials, so that many different materials may be used. For conductive structures, it may be possible to use metallization structures, silicide structures or polysilicon structures. For semiconductor regions or components, crystalline silicon may be used. For insulating portions, silicon oxide or silicon nitride may be used.

The biosensor may be formed on a purely crystalline silicon wafer or on an SOI wafer (Silicon On Insulator).

Any process technologies like CMOS, BIPOLAR, BICMOS may be implemented.

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

DESCRIPTION OF EMBODIMENTS

The illustration in the drawing is schematical. In different drawings, similar or identical elements are provided with the same reference signs.

In the following, referring to FIG. 1, a biosensor device 100 for detecting biological particles according to an exemplary embodiment of the invention will be explained.

The biosensor device 100 comprises an electromagnetic radiation transmitting member 102, namely a waveguide arrangement, adapted for transmitting electromagnetic radiation such as optical light. A plurality of sensor active structures 104 is contacted evanescently to an outer surface of the essentially cylindrical electromagnetic radiation transmitting member 102. Each of the plurality of sensor active structures 104 is sensitive to specific biological particles (for instance is sensitive only to oligonucleotides having a specific base sequence) and is adapted to modify electromagnetic radiation transmission properties of the electromagnetic radiation transmitting member 102 (for instance a wavelength of light arriving at an end thereof) in the event of the presence of the respective biological particles. The electromagnetic radiation transmitting member 102 is adapted for a simultaneous, i.e. at the same time, detection of different biological particles at different ones of the plurality of sensor active structures 104.

The electromagnetic radiation transmitting member 102 comprises a plurality of spatially separated electromagnetic radiation transmitting units 106 to 110, namely different optical fibers 106 to 110 arranged in parallel to one another, wherein each of the plurality of the sensor active structures 104 is arranged at an assigned one of the plurality of spatially separated electromagnetic radiation transmitting units 106 to 110. The sensor active structures 104 each comprise a spherical microbody 112 of silica material having a radius of 200 μm which is surrounded or covered by a layer of capture molecules 118 which are capable of performing hybridization events with particles to be detected (not shown).

An electromagnetic radiation source 114 such as one or more laser diodes 104 is provided and adapted for generating electromagnetic radiation to be coupled into the electromagnetic radiation transmitting member 102 to propagate along a propagation direction 150. More particularly, in the embodiment of FIG. 1, a light beam is coupled in a light fiber 130 having a distribution node 132 (at which an appropriate optical member may be arranged) at which the light beam is split into the various optical fibers 106 to 110. Thus, the light propagates from the electromagnetic radiation source 114 through the electromagnetic radiation transmission member 102, may be brought in interaction with the microspheres 104 mechanically connected to an outer surface of the respective fibers 106 to 110, and can then be guided to dedicated electromagnetic radiation detectors 116 such as photodiodes each adapted for detecting electromagnetic radiation after propagation along the electromagnetic radiation transmitting member 102. Thus, at each of the photodiodes 116, a corresponding electrical detection signal may be detected indicative of characteristics of the optical beam arriving at the end of the respective fiber 106 to 110. In case of an interaction between the layer of capture molecules 118 and complementary particles in an analyte, the detection signal may be characteristically modified, for instance a wavelength shift (particularly a red shift) may occur.

Furthermore, the biosensor device 100 comprises a control unit 134 (which may also be denoted as an evaluation unit) such as a microprocessor or a CPU ("central processing unit"), and which comprises processing capability allowing to control a part or the entire apparatus 100. For this purpose, the control unit 134 may be coupled for unidirectional or bidirectional data communication with the light source 114, may be coupled for unidirectional or bidirectional data communication with the photodetectors 116, and may also be coupled for unidirectional or bidirectional data communication with an input/output unit or user interface 136.

The user interface 136 may comprise input elements such as a joystick, a keypad, buttons, etc. and may also comprise an output unit such as a display, for example an LCD display or a cathode ray tube. Via the communication between the control unit 134 and the user interface 136, the user operating the user interface 136 may provide the control unit 134 with control commands, or may receive detection results from the control unit 134.

The control unit 134 may evaluate the detection signals by an appropriate evaluation algorithm allowing determining or quantifying a specific particle in the analyte from the detection signals. For instance, a wavelength shift and/or an amplitude modification may be determined allowing concluding detection information.

The biosensor device 100 may be adapted for DNA sequencing based on an evaluation of hybridization events between the plurality of sensor active structures 104 and the biological particles. With the parallel arrangements of the fibers 106 to 110, the individual excitation of whispering gallery modes in each of the fibers 106 to 110 is enabled so that a simultaneous detection of different biological particles is enabled, each of the functionalizations 118 being specifically sensitive to a complementary biological particle.

Figure 1:
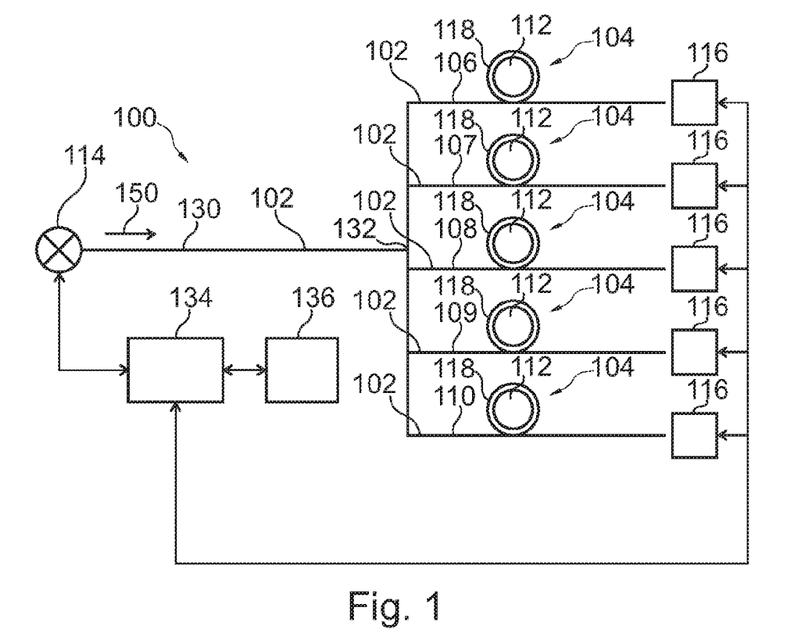
FIG. 1 to FIG. 4 show biosensor devices according to exemplary embodiments of the invention.

Before carrying out a detection, each of the silica microspheres 112 is first functionalized with a corresponding functionalization 118, the functionalizations 118 of the different microspheres 104 shown in FIG. 1 being different. This may be made possible by providing different functionalization material to each individual one of the microspheres 112 attached to the respective fibers 106 to 110. After that, the electromagnetic radiation source 114 may be triggered to generate electromagnetic radiation propagating along the electromagnetic radiation transmission member 102. When a hybridization event between a fraction of a fluidic sample and a specific one of the capture molecules 118 of the sensor active structures 104 occurs, whispering gallery modes may be excited in the respective microsphere 112 or optical fiber 106 to 110, which can be detected as a change of the detection signal at the respective one of the photodiodes 116. Thus, the analysis of the detection signals of the photodiodes 116 by the control unit 134 may allow to derive information about the biological sample, for instance may allow for DNA sequencing. Such an analysis result may be output via the input/output unit 136.

Figure 2:
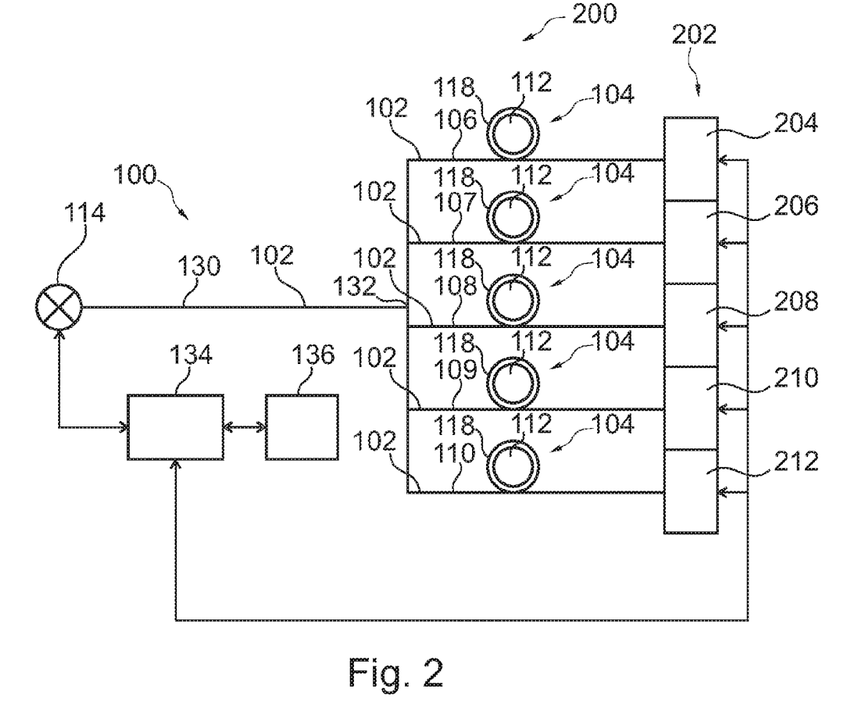

FIG. 2 shows a biosensor device 200 according to another exemplary embodiment of the invention.

The biosensor device 200 differs from the biosensor device 100 particularly in that a CCD detector 202 having segments 204, 206, 208, 210, 212 is provided, substituting the individual photodiodes 116. Thus, a one- or two-dimensional detector 202 may be connected to output ends of the optical fibers 106 to 110. Thus, with a single component 202, a one- or two-dimensional detection of a one- or two-dimensional array of optical fibers 106 to 110 is made possible.

For a one-dimensional architecture, the ends of the fibers 106 to 110 may be arranged along a straight line. For a two-dimensional architecture, an array of optical fibers may be provided within the paper plane of FIG. 2, and perpendicular thereto.

In the following, referring to FIG. 3, a biosensor device 300 according to another exemplary embodiment of the invention will be explained.

Figure 3:
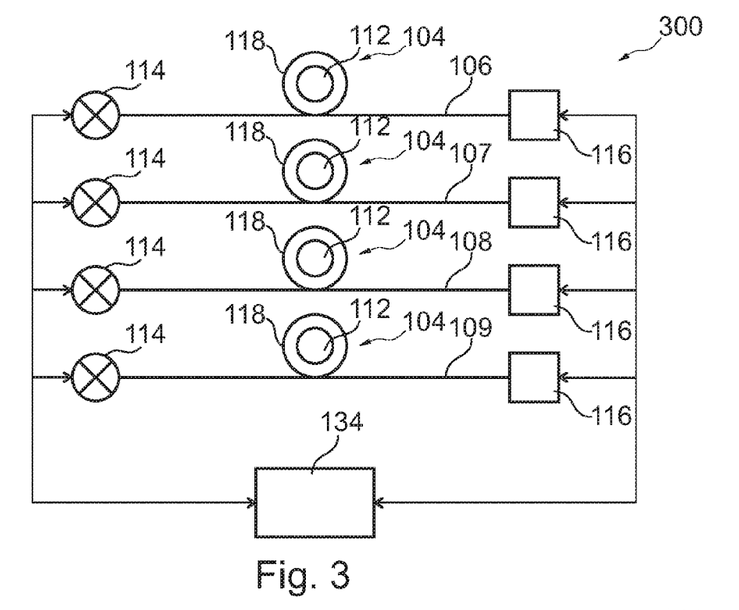

The embodiment of FIG. 3 differs from the embodiment of FIG. 1 particularly in that an individual electromagnetic radiation source 114 is provided for each individual one of the optical fibers 106 to 109, and in that the number of optical fibers is four instead of five. The separate provision of individual electromagnetic radiation sources 114 may allow for an individual control of the electromagnetic transmission properties for each individual one of the fibers 106 to 110. For example, each of the different optical fibers 106 to 109 may be provided with electromagnetic radiation of a different wavelength (and/or of a different intensity), allowing to use a single detector being wavelength dependent.

In the following, referring to FIG. 4, a biosensor device 400 according to another exemplary embodiment of the invention will be explained.

Figure 4:
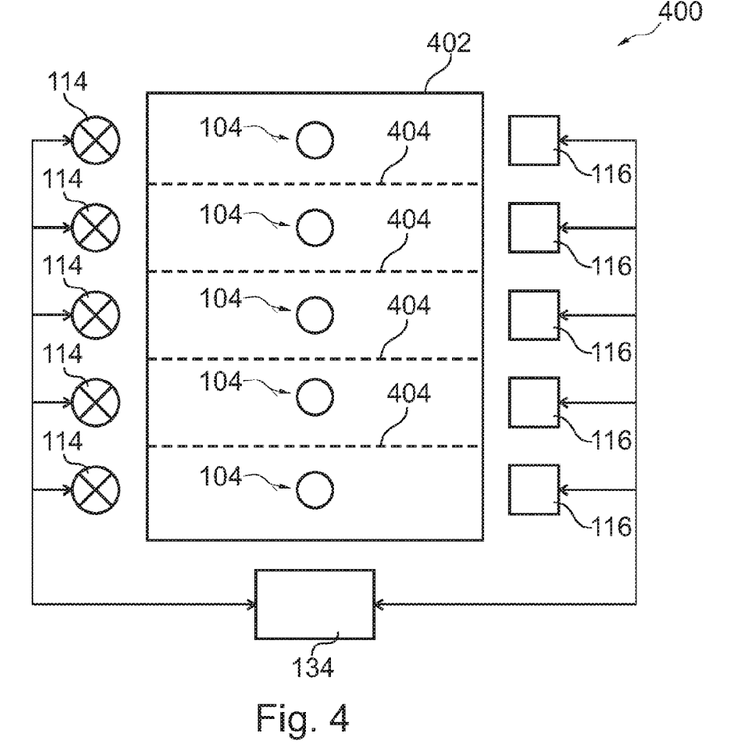

The embodiment of FIG. 4 differs from the embodiment of FIG. 3 particularly in that five instead of four parallel paths are possible, and more important in that the optical fibers 106 to 109 are substituted by a thin planar continuous silica plate 402 which is arranged between the electromagnetic radiation sources 114 and the photodiodes 116 in such a manner that five different optical paths without or essentially without crosstalk are made possible. FIG. 4 shows a top view of the plate 402 and shows the functionalized microspheres 104 fixedly connected to an upper surface of the plate 402, to trigger whispery gallery modes.

In order to reliably decouple the individual optical paths in FIG. 4, it is optionally possible to provide walls 404 between adjacent paths with an optically reflective or absorbing material.

In the following, methods for DNA sequencing by hybridization (SBH) will be explained.

Next, a general model for SBH will be explained.

In a first step, namely a biochemical step, a chip named microarray may be provided for detecting all k-mers at a given unknown (target) DNA sample. This step may be referred as hybridization. The set of k-mers may be referred as a spectrum. Each k-mer may be referred as a probe.

In a second step, namely a combinatorial step, an algorithmic reconstruction of an original sequence from the set of k-mers may be provided. For this purpose, conventionally a chip may be prepared with different k-mers (k-mer may refer to, for example, TGT, TGA, TGG, CTT, CTG, CTA, GAA, GAT, GAC). When a sample is brought in contact with such a chip or array, the labeled target DNA sequence may hybridize to the k-mers, when the k-mers are complementary to the capture molecules being oligonucleotides.

Next, it is possible to get rid of the target DNA that did not hybridize with the probe k-mers. In this case, it is possible to get rid of these probes by washing them away. Subsequently, the labeled target DNA may be detected that remains. For example, capture probes having a CTG sequence are complementary to biological probes having a GAC sequence. From the resulting spectrum, by implementing computer algorithms that the skilled person knows as such, target sequence reconstruction is possible. The ensemble of the k-mers that hybridized may be denoted as the spectrum. Thus, by applying the computer algorithms, it is possible to reconstruct the target sequence from the spectrum obtained.

However, such a conventional approach involves a number of drawbacks, particularly that sample preparation and hybridization chips is costly and slow, highly skilled workers are needed for sample preparation, detection levels require PCR (polymerase chain reaction) amplification of DNA (target and k-mers), and labeling for readout is costly and subjected to errors.

Based on the above recognitions regarding SBH, the present inventor has developed the exemplary embodiments described herein that are based on the so-called whispering gallery mode detection method.

Figure 5:
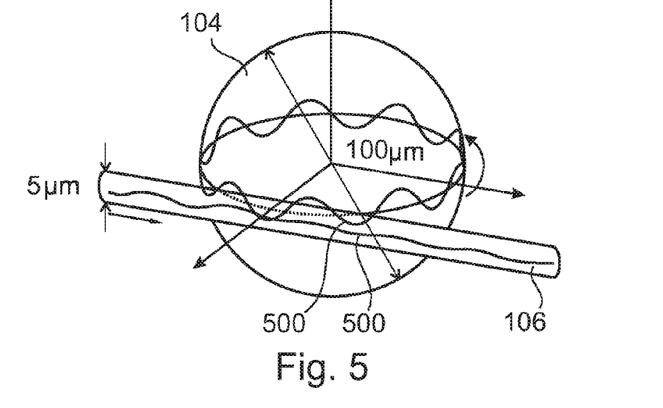
FIG. 5 shows an enlarged view of a microsphere coupled to an optical fiber as a basis for a WGM detection according to an exemplary embodiment of the invention.

FIG. 5 illustrates the whispering gallery mode detection method on the basis of a cylindrical optical fiber 106 having attached thereto a silica microsphere 104. A propagating electromagnetic radiation beam 500 is shown which involves a characteristic interaction between the microsphere 104 and the fiber 106.

The whispering gallery mode (WGM) is a particular mode of micro cavity resonances. It occurs when light 500 at certain frequencies travels in a dielectric medium 104 of circular geometry. After repeated total internal reflections at the curved boundary, the electromagnetic field can close on itself, giving rise to resonances.

According to exemplary embodiments of the invention, the WGM is applied particularly to DNA sequencing.

Figure 6:
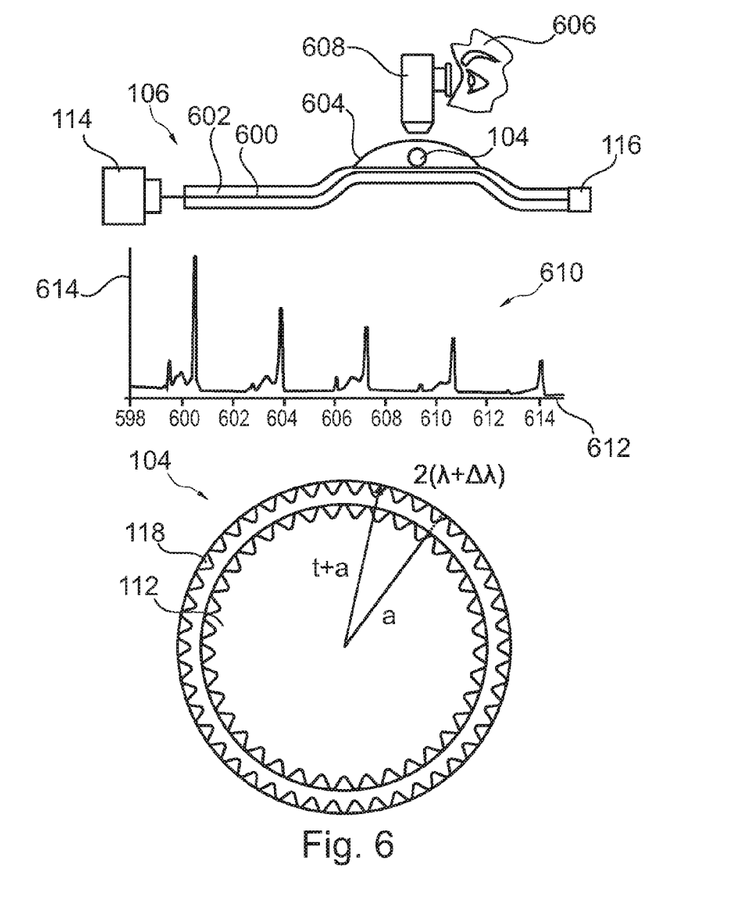
FIG. 6 illustrates a method of performing a WGM detection according to an exemplary embodiment of the invention.

FIG. 6 shows a schematic illustration of how WGM works.

A laser 114 couples light into an optical fiber 106 having a core 600 and a cladding 602. A water droplet 604 is shown in which a microsphere 104 is provided in functional contact with the optical fiber 106. A user 606 may monitor the coupling procedure via a microscope 608.

First, a silica microsphere 104 is coupled to an optic fiber 106. The fiber 106 is then illuminated with a laser 114. The resonance peaks (modes in the sphere 104) are then detected as spectrum peaks.

FIG. 6 further shows a schematic diagram 610 having an abscissa 612 along which a wavelength is plotted in nm and having an ordinate 614 along which an intensity is plotted in arbitrary units.

FIG. 6 also shows an enlarged view of a functionalized microsphere 104 comprising the spherical silica body 112 and a surrounding protein or oligonucleotide layer 118.

When the silica sphere 112 of radius "a" is coated with a biomolecule having a thickness "t", the coating changes the radius to a+t and therefore shifts the resonance peak of this sphere from $\lambda$ to $\lambda+\Delta\lambda$. Thus, the presence of a biomolecule can be detected as a change of the resonance peak in the spectrum.

Figure 7:
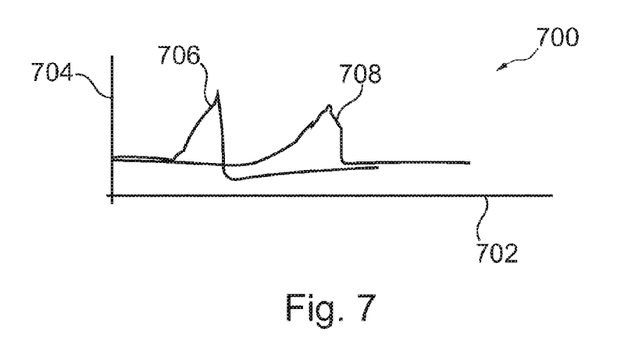
FIG. 7 illustrates a detection spectrum according to an exemplary embodiment of the invention.

FIG. 7 shows such an exemplary spectrum 700 having an abscissa 702 along which a wavelength is plotted, and having an ordinate 704 along which an intensity is plotted. A first curve 706 relates to a situation in which no biomolecule is attached to the microsphere 104. A second curve 708 relates to a scenario in which a biomolecule is attached to the microsphere 104, so that a (red) shift in the resonant frequency is detectable.

According to an exemplary embodiment of the invention, WGM may be used for DNA sequencing by hybridization, involving particularly the advantages of increasing sensitivity so that a minimum amplification may be sufficient, avoiding the use of labels for detection to obtain a cost reduction, integrating such a system easily with CMOS technology, avoiding false readouts due to label detection, and simplifying the sample preparation steps significantly.

Again referring to the embodiment of FIG. 1, the microsphere 104 connected to the first optical fiber 106 may be coated with a k-mer 1 (i.e. ACG), the microsphere 104 connected to the second optical fiber 107 may be coated with a k-mer 2 (i.e. CGC), the microsphere 104 fixed to the third optical fiber 108 may be coated with a k-mer 3 (i.e. GCA), the microsphere 104 connected to the fourth optical fiber 109 may be coated with a k-mer 4 (i.e. CAT), and the fifth optical fiber 105 to which the corresponding microsphere 104 is attached is coated with k-mer 5 (i.e. ATC).

As a first step, the device 100 may be prepared as shown in FIG. 1. Next, a hybridization of the target sequence may be triggered. This target sequence to be detected is a priori unknown, but for this example is assumed to be ACGCATC). Then, after the performance of the hybridization assay, each end of the optical fibers 106 to 110 is interrogated. The k-mers 118 that hybridized with the target sequence are detected as a shift in the resonance peaks of each sphere 104. The k-mers that did not hybridize will not cause a shift of the peaks of the spheres. Computer algorithms (such as the conventionally known computer algorithms) may be used to reconstruct the targeted sequence from the k-mer spectrum.

Figure 8:
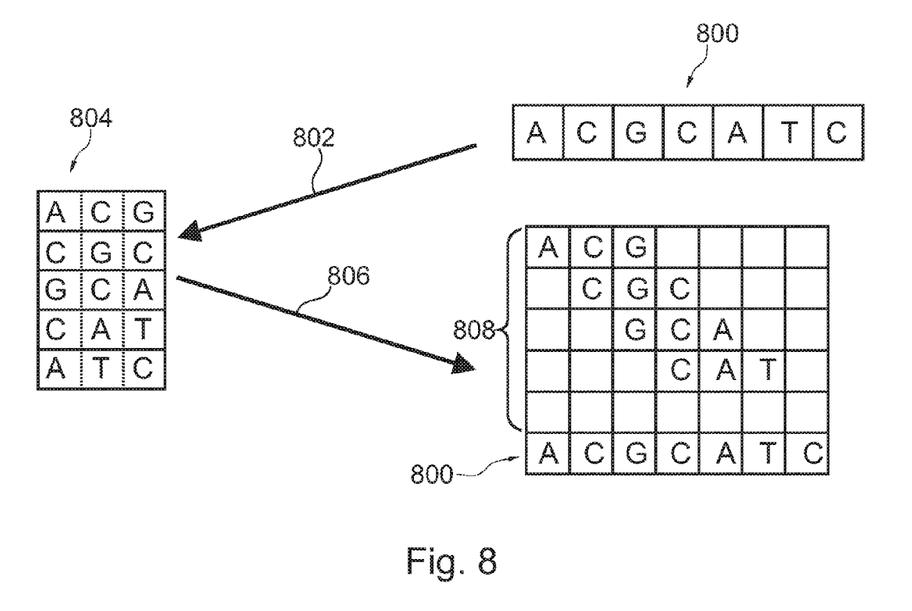
FIG. 8 schematically illustrates a method of DNA sequencing according to an exemplary embodiment of the invention.

This will be illustrated in more detail in FIG. 8.

In FIG. 8, the sequence of the DNA sample is denoted with reference numeral 800. Via a hybridization procedure 802, a spectrum of the example after interrogation is obtained, which is denoted with reference numeral 804. In a reconstruction procedure 806, the sequence 800 is reconstructed from individual sequence portions 808 obtained from the various fibers 106 to 110. In other words, the sequence 800 is reconstructed from the spectrum of the example.

Figure 9:
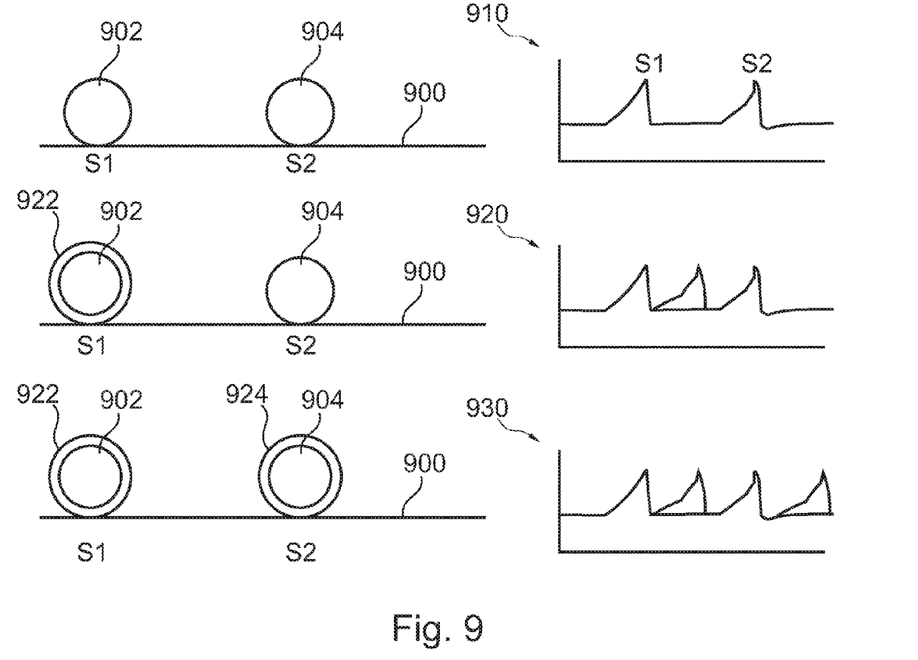
FIG. 9 illustrates a conventional detection scheme.

FIG. 9 shows a conventional approach having a single optical fiber 900 having attached thereto two different microspheres 902, 904. The corresponding signals in the spectrum are shown in a schematic spectrum 910. As shown in a spectrum 920, a detection event occurs at the first microsphere 902 being surrounded by a jacket 922. A third spectrum 930 relates to a situation in which a mantle 922 covers the first microsphere 902 and the second microsphere 904 is coupled by a mantle 924. As can be taken from the spectrum 920, S1 shifts due to the biomolecules, while S2 remains (or vice versa). The third diagram 930 shows that S1 and S2 shift.

The shifts of S1 and S2 may be different according to the types of biomolecules that are coated. Thus, it may be possible, only in a simple scenario, to distinguish specific types of biomolecules attached to individual spheres.

Finally, it should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The words "comprising" and "comprises", and the like, do not exclude the presence of elements or steps other than those listed in any claim or the specification as a whole. The singular reference of an element does not exclude the plural reference of such elements and vice-versa. In a device claim enumerating several means, several of these means may be embodied by one and the same item of software or hardware. The mere fact that certain measures are recited in mutually different dependent claims does not indicate that a combination of these measures cannot be used to advantage.

The invention claimed is:

1. A biosensor device for detecting biological particles, the biosensor device comprising
   a plurality of electromagnetic radiation sources;
   a plurality of optical paths formed in a planar continuous silica plate, and a plurality of optically reflective or absorptive walls disposed between adjacent optical paths of the plurality of optical paths;
   wherein each of the plurality of optical paths is coupled to a corresponding electromagnetic radiation source, wherein each of the plurality of optical paths is configured to transmit electromagnetic radiation from the corresponding electromagnetic radiation source through the optical path; and
   a plurality of sensor active structures coupled with the planar continuous silica plate, wherein a one of the plurality of sensor active structures is coupled to and corresponds with each of the plurality of optical paths;
   wherein each of the plurality of sensor active structures is sensitive to specific biological particles and modifies at least one electromagnetic radiation transmission property of the corresponding optical path in the event of the presence of the respective biological particles at the sensor active structure;
   wherein each of the plurality of sensor active structures at the plurality of optical paths facilitates simultaneous detection of different biological particles at each of the plurality of optical paths.

2. The biosensor device of claim 1, wherein the plurality of optical paths are aligned in parallel.

3. The biosensor device of claim 1, wherein each of the plurality of sensor active structures comprises a silica microsphere.

4. The biosensor device of claim 1, comprising an electromagnetic radiation detector to detect electromagnetic radiation after propagation along the plurality of optical paths.

5. The biosensor device of claim 1, comprising one or more capture molecules arranged at a surface of each of the plurality of sensor active structures and being adapted for interacting with the biological particles.

6. The biosensor device according to claim 1, comprising an evaluation unit to evaluate the detection to thereby identify the biological particles.

7. The biosensor device according to claim 1, manufactured in CMOS technology.

8. A biosensor device for detecting biological particles, the biosensor device comprising:
   a plurality of optical paths to transmit electromagnetic radiation, the plurality of optical paths formed in a planar continuous silica plate, and a plurality of optically reflective or absorptive walls disposed between adjacent optical paths of the plurality of optical paths;
   a plurality of sensor active structures coupled with the planar continuous silica plate, wherein a one of the plurality of sensor active structures is coupled with each of the plurality of optical paths;
   wherein each of the plurality of sensor active structures is sensitive to specific biological particles to modify electromagnetic radiation transmission properties of a corresponding one of the plurality of optical paths in response to the presence of the respective biological particles; and
   a plurality of electromagnetic radiation detectors coupled to the sensor active structures to simultaneously detect different biological particles at different ones of the plurality of sensor active structures.

9. The biosensor device of claim 8, comprising a plurality of electromagnetic radiation sources to generate electromagnetic radiation, each of the plurality of electromagnetic radiation sources to be coupled with a corresponding one of the plurality of optical paths.

* * * * *